United States Patent
Mino Sotelo De Kaspar et al.

(10) Patent No.: US 7,621,278 B2
(45) Date of Patent: Nov. 24, 2009

(54) EYE DRAPE FOR SURGICAL PROCEDURES

(76) Inventors: Herminia Mino Sotelo De Kaspar, Angermaierstrasse 14, Weilheim (DE) 82362; James Craig Milroy, 184 Heather La., Palo Alto, CA (US) 94303; Peter Roy Egbert, 1095 Trinity Dr., Menlo Park, CA (US) 94025

( * ) Notice: Subject to any disclaimer, the term of this patent is extended or adjusted under 35 U.S.C. 154(b) by 0 days.

(21) Appl. No.: 11/264,296

(22) Filed: Oct. 31, 2005

(65) Prior Publication Data
US 2006/0102187 A1    May 18, 2006

Related U.S. Application Data

(60) Provisional application No. 60/624,220, filed on Nov. 1, 2004.

(51) Int. Cl.
*A61F 5/37* (2006.01)
*A61F 11/00* (2006.01)
*A61F 9/00* (2006.01)
*A61B 19/08* (2006.01)

(52) U.S. Cl. .............. 128/853; 128/846; 128/849; 128/850; 128/851; 128/852; 128/857; 128/858

(58) Field of Classification Search ........ 128/849–853, 128/858, 846, 857
See application file for complete search history.

(56) References Cited

U.S. PATENT DOCUMENTS

| | | | |
|---|---|---|---|
| 5,213,114 A | 5/1993 | Bailey, Jr. | 128/849 |
| 5,632,284 A | 5/1997 | Graether | 128/849 |
| 6,269,815 B1 | 8/2001 | Jascomb | 128/849 |
| 6,675,805 B1 | 1/2004 | Graether | 128/849 |
| 2002/0108615 A1* | 8/2002 | Levitt et al. | 128/853 |
| 2006/0124139 A1* | 6/2006 | Morris | 128/849 |

OTHER PUBLICATIONS

Slade et al. "Draping Technique to Isolate Lashes and Achieve Maximum Exposure" (1998) Published in J. Cataract Refreact Surg vol. 24 p. 1030-1031.

* cited by examiner

*Primary Examiner*—Patricia M Bianco
*Assistant Examiner*—Tarla R Patel
(74) *Attorney, Agent, or Firm*—Lumen Patent Firm

(57) ABSTRACT

Eye drapes that cover the conjunctiva and reduce the incidence of eye infection are provided. The eye drape has a flexible material and attached thereto a surgical drape. The flexible material is preferably circular with an opening to expose the cornea. The bottom of the flexible material is preferably convex relative to the shape of the eye. The outer diameter of the flexible material is conveniently fits over the ball of the eye. The surgical drape has an opening greater than or equal to the inner diameter and smaller than or equal to the outer diameter of the flexible material. The flexible material is removably fixed to the eye through a vacuum force caused by air expelled from, e.g. (i) a pocket of air in between the flexible material and the eye, (ii) a chamber with openings at the bottom of the flexible material, and/or (iii) a suction device.

9 Claims, 4 Drawing Sheets

EYE DRAPE FOR SURGICAL PROCEDURES

CROSS-REFERENCE TO RELATED APPLICATIONS

This application is cross-referenced to and claims benefit from U.S. Provisional Application 60/624,220 filed Nov. 1, 2004, which is hereby incorporated by reference.

FIELD OF THE INVENTION

The invention relates generally to ophthalmology. More particularly, the invention relates to an eye drape for reducing the incidence of eye infection following surgery.

BACKGROUND OF THE INVENTION

Drapes can be useful during examination or surgery on various parts of the body. The drapes give the healthcare provider access for examination. In case of a surgery, the drapes give the surgeon access to the surgical field while generally isolating that part of the body from other body parts. Accordingly, drapes usually help reduce the chances of infection occurring after examination or surgery.

Draping the human eye is, however, particularly difficult due in part to the small size and intricate structure of the human eye. Laying a drape sheet over the eye and providing an access opening therein still leaves the eyelids in the surgical field. Generally it is desirable to retract the eyelids to provide greater access to the eyeball. It is also desirable to remove the eyelids and eyelashes from the surgical field. Examples of such drapes are disclosed in U.S. Pat. Nos. 5,632,284, 5,213,114 and 6,675,805. However, these drapes do not prevent bacteria from the majority of the bulbar conjunctiva from entering the eye.

Sterilization of the conjunctiva could be used, however, the nature of the conjunctiva makes it difficult to sterilize before surgery. The peripheral conjunctiva, including the fornices, the caruncle, and the lining inside of the lids, has many crypts and folds not reached by antiseptic solutions.

Accordingly, it would be considered an advance in the art to provide new eye drapes that cover the conjunctiva and therewith reduce the incidence of eye infection following eye examination or surgery.

SUMMARY OF THE INVENTION

The present invention provides new eye drapes that cover the conjunctiva and therewith reduce the incidence of eye infection following eye examination or surgery. The eye drape is a combination of a flexible material and a surgical drape attached to the flexible material. The flexible material has a circular shape with a central opening through which an eye examination or surgery can be conducted. The central opening has a diameter large enough to expose the cornea of the eye. The outer diameter of the flexible material is large enough to conveniently fit over the ball of the eye. The flexible material preferably has a curvature that is convex or slightly convex relative to the curvature of the eye.

The surgical drape has an opening greater than or equal to the inner diameter of the flexible material and smaller than or equal to the outer diameter of the flexible material. The size of the surgical drape is large enough to cover at least the area around the eye.

The flexible material distinguishes two positions. The first position of the flexible material has a curvature that is convex relative to the curvature of the eye. The flexible material is placed over the eye in the first position such that a pocket of air is created in between the space of the flexible material and the eye. In the second position of the flexible material the convexity of the curvature is reduced relative to the curvature of the eye. The flexible material is fixed to the eye through a vacuum force caused by air expelled from the pocket.

The flexible material could have a chamber with a plurality of openings at the bottom. In this case, the chamber in the first position of the flexible material contains air, which is expelled from the chamber via some or all of the openings. The flexible material is fixed to the eye through a vacuum force caused by air expelled from the chamber.

The flexible material could further have at least one opening at the top site or its lateral site that is in contact with the chamber. The opening is connected to an air suction device capable of expelling air from the chamber and changing the position of the flexible material from its first position to its second position.

BRIEF DESCRIPTION OF THE DRAWINGS

The objectives and advantages of the invention will be understood by reading the following detailed description in conjunction with the drawings, in which.

DETAILED DESCRIPTION

Figure 1:
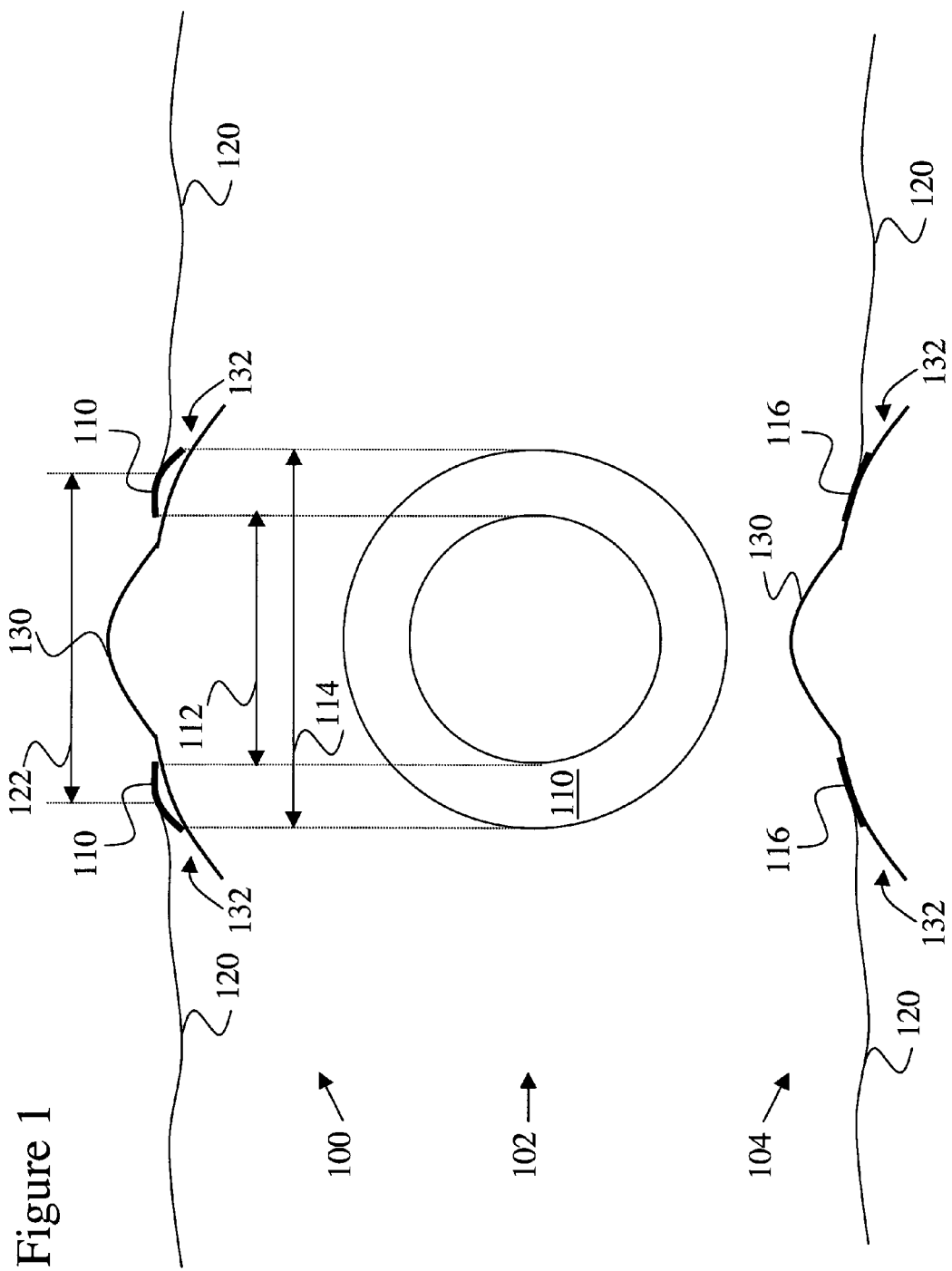
FIG. 1 shows an eye drape with cross-sectional views 100 and 104 and a top view 102 according to a first embodiment of the present invention.

The key idea of the eye drape of the present invention is to reduce the incidence of an eye infection following an examination or a surgery of an eye. FIG. 1 shows a first embodiment of eye drape 100 with a flexible material 110 and a surgical drape 120. The eye drape, as a combination of flexible material and surgical drape, is intended to cover at least the conjunctiva, the eyelids, eyelashes, and lid margins.

Flexible material 110 has a substantially circular shape as shown by 102 and includes a central opening with an inner diameter 112 through which an eye examination or eye surgery can be conducted. In one example inner diameter 112 is large enough to expose the cornea 130 of the eye. Examples of reasonable inner diameters range from about 13 to about 16 mm. Flexible material 110 has an outer diameter 114 large enough to conveniently fit over the ball 132 of the eye. Examples of reasonable outer diameters range from about 25 to about 30 mm. The thickness of flexible material 110 is about 1 to 4 mm, and should be thin enough so as not to impede the surgical instruments during the operation. In a variation a ridge is added to the top (away from the eye) of the flexible material to enhance the watertight barrier function.

Figure 2:
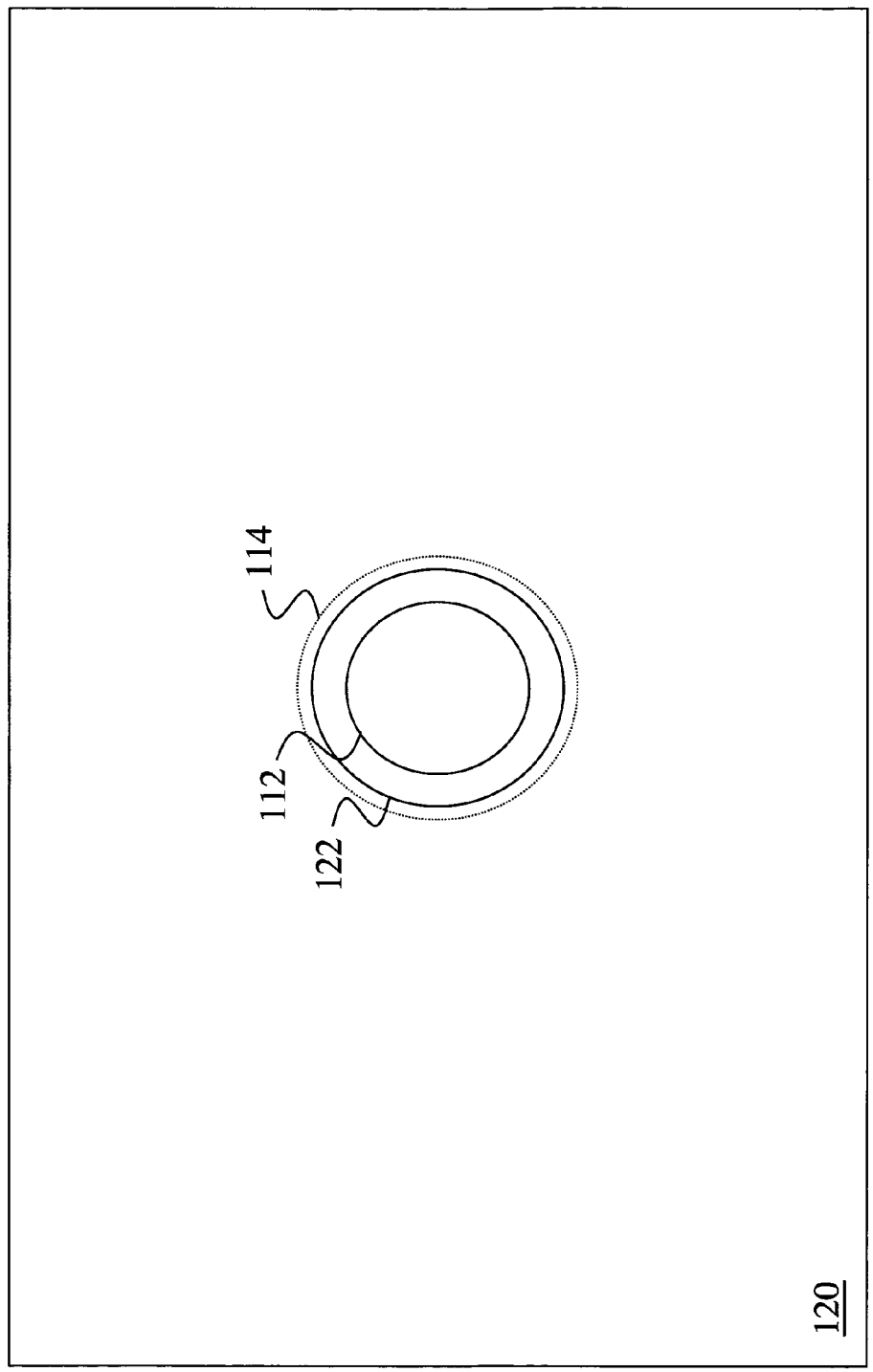
FIG. 2 shows a top view of the eye drape according to the present invention.

Surgical drape 120 is attached to flexible material 110. It has an opening 122 greater than or equal to inner diameter 112 of the flexible material and smaller than or equal to outer diameter 114 of flexible material as shown in FIGS. 1-2. The size of surgical drape 120 is large enough to cover at least the area around the eye. The flexible material covers (part of) the conjunctiva, whereby the surgical drape covers at least the eyelids, eyelashes, and lid margins. The surgical drape is preferably a standard ophthalmic sterile surgical drape of hypoallergenic plastic material used to cover the head. It is attached to the flexible material by an adhesive or glue that preferably provides a watertight connection.

Flexible material 110 has a first position in which it has a curvature that is convex relative to the curvature of the eye (See side view 100 in FIG. 1). The flexible material 110 is placed over the eye (e.g. exposing the cornea through the central opening) in this first position. The curvature allows for a pocket of air in between the space of flexible material 110 and the ball of the eye 132. Flexible material has a second position (in side view 104 and shown by 116) in which the convexity of the curvature is reduced relative to the curvature of the eye. Pressing down flexible material onto the ball of the eye reduces the convexity; i.e. flexible material 110 in position 116 is fixed to the eye through a vacuum force caused by the air expelled from the original pocket. The material of the flexible material must be flexible to conform to eye deformation, yet firm enough to withstand a (partial) vacuum without collapsing. Examples of suitable materials are semi-flexible plastic, medical-grade silicone, or the like. The combination of material and size of the flexible material should be such to maintain the best suction force (i.e. having a watertight seal) without harming the bulbar conjunctiva. Removal of the flexible material can be accomplished by pulling the surgical drape away from the eye, pealing the flexible material from the eye, or combination thereof.

Figure 3:
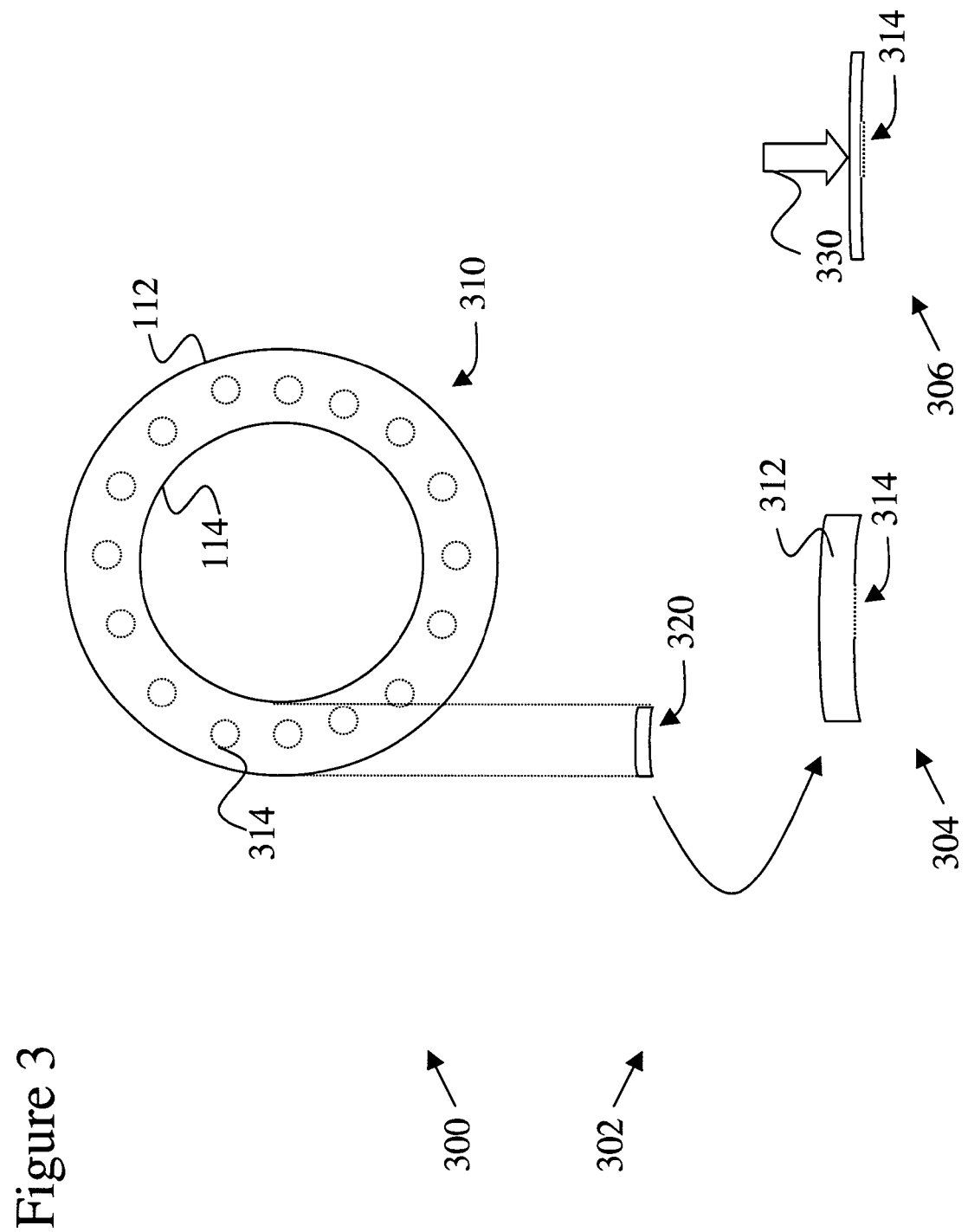
FIG. 3 shows an eye drape with a top view 300 and a cross-sectional view 302 according to a second embodiment of the present invention.

FIG. 3 shows a second embodiment of the eye drape of the present invention. This eye drape is similar to the eye drape described with respect to the first embodiment in FIGS. 1-2. The difference, however, is that the flexible material 310 in the second embodiment further includes a chamber 312 that is filled with air in the first position 304. The bottom site of flexible material 300 has a plurality of openings 314 such as holes (as shown), slits (not shown) or any other type of opening. The size and number of the openings adjacent to the conjunctiva is such to maintain the best suction (i.e. having a watertight seal) without harming the bulbar conjunctiva.

In this example, flexible material 310 has a first position 304. The bottom of flexible material could have a curvature 320 that is convex relative to the curvature of the eye, which is preferred, but not required. The flexible material 310 is placed over the eye (e.g. exposing the cornea through the central opening) in this first position whereby the chamber contains air. Flexible material has a second position shown by 306 after being pressed 330 down onto the ball of the eye. Flexible material 310 is fixed to the eye through a vacuum force caused by the air expelled which is expelled from the chamber through some or all of the openings. In case the bottom curvature was convex, the convexity is reduced relative to the curvature of the eye due to the vacuum force. Removal of the flexible material in this example is similar as to the first embodiment and can be accomplished by pulling the surgical drape away from the eye, pealing (part of) the flexible material from the eye, or combination thereof.

Figure 4:
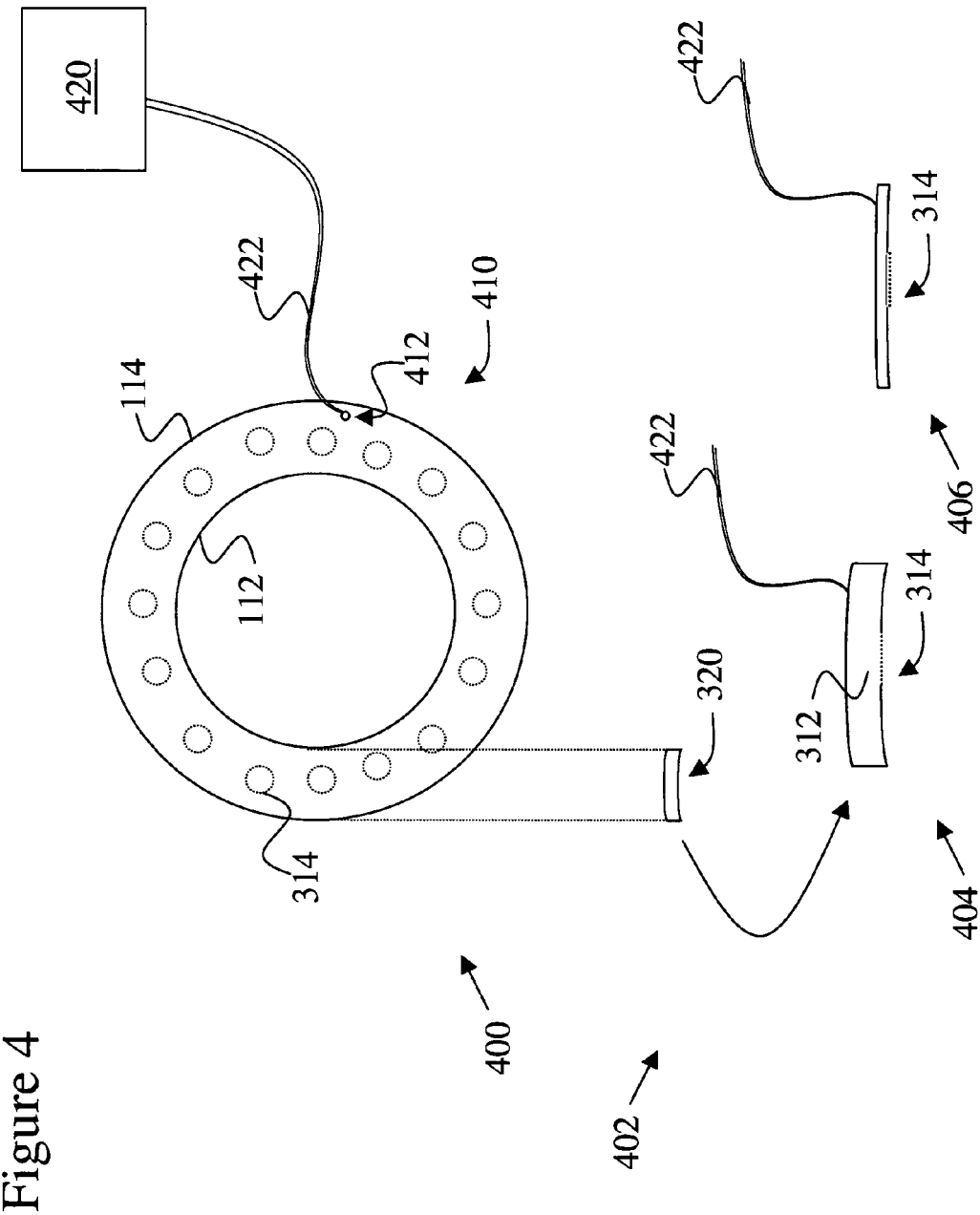
FIG. 4 shows an eye drape with a top view 400 and a cross-sectional view 402 according to a third embodiment of the present invention.

FIG. 4 shows a third embodiment of the eye drape of the present invention. This eye drape is similar to the eye drape described with respect to the first and second embodiments in FIGS. 1-3. The difference is, however, that the flexible material 410 in the third embodiment further includes at least one opening at a site (e.g. top site (as shown), lateral site (not shown)) of flexible material 410. In FIG. 4, one opening 412 is shown that has direct access to chamber 312. Instead of pressing away the air from chamber 312 through some or all of the openings as in the second embodiment, an air suction device 420 is now included that expels the air from chamber 312 via tubing 422 to change flexible material 410 from a first position 404 to a second position 406. The first and second positions are similar as described with respect to FIGS. 1 and 3. The suction device maintains the vacuum force required to maintain a watertight seal between the flexible material and the eye. Removal of the flexible material can be accomplished by pulling the surgical drape away from the eye, pealing (part of) the flexible material from the eye, releasing the vacuum force, or combinations thereof.

In one example the suction device is a syringe connected to the hole of the flexible material by a flexible tube. A vacuum is created between the flexible material and the conjunctiva when the syringe is pulled back. The vacuum could then be maintained by closing off the tube with a pinch valve or stopcock. In another example, more sophisticated vacuum pumps or suction devices could be used.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed is:

1. An eye drape for reducing the incidence of an eye infection following an examination or a surgery of an eye, comprising:
   a. a flexible material with a substantially circular shape, wherein said flexible material comprises:
      (i) a central opening with an inner diameter therein, through which said examination or said surgery of said eye can be conducted,
      (ii) an outer diameter large enough to conveniently fit over the ball of said eye,
      (iii) a first position wherein said flexible material has a curvature that is convex relative to the curvature of said eye such that when said flexible material is placed over said eye a pocket of air is created in between the space of said flexible material and said eye, and
      (iv) a second position wherein said convexity of said curvature is reduced relative to said curvature of said eye when said flexible material is pressed onto said eye and whereby said flexible material in said second position is being fixed to said eye through a vacuum force caused by air expelled from said pocket; and
   b. a surgical drape attached to said flexible material, wherein said drape comprises:
      (i) an opening greater than or equal to said inner diameter of said flexible material and smaller than or equal to said outer diameter of said flexible material, and
      (ii) a size large enough to cover at least the area around the eye.

2. The eye drape as set forth in claim 1, wherein said inner diameter of said flexible material is large enough to expose the cornea of said eye.

3. The eye drape as set forth in claim 1, wherein said inner diameter of said flexible material is about 13 to about 16 mm.

4. The eye drape as set forth in claim 1, wherein said outer diameter of said flexible material is about 25 to about 30 mm.

5. A method of using an eye drape for reducing the incidence of an eye infection following an examination or a surgery of an eye, comprising:
   a. having a flexible material with a substantially circular shape, wherein said flexible material distinguishes an outer border and an inner border, and wherein said inner border defines a central opening through which said examination or said surgery of said eye can be conducted, wherein said outer border is large enough to conveniently fit over the ball of said eye, wherein said flexible material distinguishes a first position in which said flexible material has a curvature that is convex relative to the curvature of said eye, and a second position in which said convexity of said curvature is reduced relative to that of said first position;

b. placing said flexible material over said eye with said flexible material in said first position such that a pocket of air is created in between the space of said curved flexible material and said eye; and c. pressing said flexible material onto said eye whereby said flexible material changes from said first position into said second position such that said flexible material is being fixed onto said eye through a vacuum force caused by air expelled from said pocket when said flexible material changes from said first position to said second position.

6. The method as set forth in claim 5, further comprising having a surgical drape attached to said flexible material without obstructing said central opening and large enough to cover at least the area around the eye.

7. The method as set forth in claim 5, wherein said inner diameter of said flexible material is large enough to expose the cornea of said eye.

8. The method as set forth in claim 5, wherein said inner diameter of said flexible material is about 13 to about 16 mm.

9. The method as set forth in claim 5, wherein said outer diameter of said flexible material is about 25 to about 30 mm.

* * * * *